US00PP24729P3

(12) United States Plant Patent
Glen

(10) Patent No.: US PP24,729 P3
(45) Date of Patent: Aug. 5, 2014

(54) PEACH TREE NAMED 'RED PRINCESS'

(50) Latin Name: *Prunus persica*
Varietal Denomination: Red Princess

(71) Applicant: Lowell Glen, Le Grand, CA (US)

(72) Inventor: Lowell Glen, Le Grand, CA (US)

( * ) Notice: Subject to any disclaimer, the term of this patent is extended or adjusted under 35 U.S.C. 154(b) by 29 days.

(21) Appl. No.: 13/694,608

(22) Filed: Dec. 13, 2012

(65) Prior Publication Data

US 2014/0173794 P1 Jun. 19, 2014

(51) Int. Cl.
*A01H 5/00* (2006.01)

(52) U.S. Cl.
USPC ..... Plt./197

(58) Field of Classification Search
CPC .. A01H 5/0868; A01H 5/0856; A01H 5/0837
USPC ..... Plt./197
See application file for complete search history.

(56) References Cited

U.S. PATENT DOCUMENTS

PP8,948 P 10/1994 Bradford
PP14,695 P2 4/2004 Bradford

*Primary Examiner* — Kent L Bell

(57) ABSTRACT

The present invention relates to a new and distinct variety of peach tree, *Prunus persica*, broadly characterized by a medium size, moderately vigorous, hardy, self-fertile, productive and regular bearing tree. The variety blooms during the mid season and requires about 600 chilling hours. The fruit matures under the ecological conditions described in late June, with first picking on Jun. 27, 2012. The fruit is uniformly large in size, acidic with traditional peach flavor, nearly globose in shape, clingstone in type, firm in texture, yellow in flesh color, virtually full red in skin color, and has a sweet kernel.

1 Drawing Sheet

Botanical classification: *Prunus persica.*
Variety denomination: 'RED PRINCESS'.

BACKGROUND OF THE VARIETY

In a continuing effort to improve the quality of shipping fruits, I, the inventor, typically hybridize a large number of peach, nectarine, plum, apricot, and cherry seedlings each year. I also grow a smaller number of open pollinated seeds of each of these fruits, usually to capture recessive traits. The present invention relates to a new and distinct variety of peach tree, which has been denominated varietally as 'Red Princess'.

In 2004 I made a first generation hybridization using 'Diamond Ray' (U.S. Plant Pat. No. 8,948) nectarine as the selected seed parent and an unnamed peach as the selected pollen parent. The fruit of this cross was gathered that summer, and the seeds were removed, cracked, stratified, germinated, and grown as seedlings on their own root in my greenhouse facility. Upon reaching dormancy I transplanted them to a cultivated area of my experimental orchard located near Le Grand, Calif., in Merced County (San Joaquin Valley). During the fruit evaluation season of 2008 I selected the present variety as a single tree from the group of seedlings described above. Subsequent to origination of the present variety of peach tree, I asexually reproduced it by budding and grafting in the experimental orchard described above, and such reproduction of tree and fruit characteristics were true to the original tree in all respects. The reproduction of the variety included the use of 'Nemaguard' (unpatented) rootstock upon which the present variety was compatible and true to type.

While the present variety is similar to its seed parent, 'Diamond Ray', in several aspects, such as producing fruit that is full red in skin color, yellow in flesh color, and firm in texture, it is quite distinguished from it by being a peach instead of nectarine.

While the present variety is similar to its unnamed pollen parent in several aspects, such as producing peaches that are nearly full red in skin color, yellow in flesh color, and firm in texture, it is quite distinguished therefrom by requiring a higher amount of chill portions and by producing peaches that are much larger in size and that mature about 50 days later.

The present variety is most similar to 'Bright Princess' (U.S. Plant Pat. No. 14,695) peach by being self-fruitful, having large blossoms, having reniform leaf glands, and producing an abundance of yellow flesh peaches that are firm, that are nearly full red in skin color, and that have a sweet kernel, but is distinguished therefrom by requiring more chilling hours, by blooming later in the season, and by producing fruit that is somewhat larger in size, clingstone rather than freestone in type, and that matures about ten days later.

SUMMARY OF VARIETY

In summary, the present variety is characterized by a medium size, moderately vigorous, hardy, self-fertile, productive and regular bearing tree. The variety blooms during the mid season and requires about 600 chilling hours. The fruit matures under the ecological conditions described in late June, with first picking on Jun. 27, 2012. The fruit is uniformly large in size, acidic with traditional peach flavor, nearly globose in shape, clingstone in type, firm in texture, yellow in flesh color, virtually full red in skin color, and has a sweet kernel.

DRAWING

The accompanying photograph consists of four whole fruits positioned to display the characteristics of the skin color and form, one sliced fruit to reveal the flesh and stone, two insets to reveal buds and blossoms, typical leaves, and a tip shoot.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on Jul. 2, 2012, on the original tree during its eighth growing season. The blossom and flower descriptions were made the previous blooming season. All major color code designations are by reference to the Inter-Society Color Council, National Bureau of Standards. Common color names are also used occasionally.

PARENTAGE

Seed parent: 'Diamond Ray' (U.S. Plant Pat. No. 8,948).
Pollen parent: Unnamed peach.

TREE

Size: Medium, reaching and maintaining a height of 8' [2.44 m.] and a spread of 6' [1.83 m.] after eight growing seasons utilizing typical dormant pruning.
Vigor: Medium vigor, responding typically to irrigation and fertilization. The variety grows about 3' [0.91 m.] of surplus top-growth during the spring and summer. The plant should be grown on a standard commercial rootstock for production purposes.
Growth: Spreading and dense.
Form: Pruned to a vase form.
Hardiness: Hardy with respect to central California winters.
Chilling requirement: About 600 hours.
Heat tolerance: Observed to perform adequately in typical central California climatic conditions, which typically include extended periods of heat.
Drought tolerance: Variety is developed for commercial orchards and requires regular irrigation.
Production: Productive, thinning usually necessary.
Fertility: Self-fertile.
Bearing: Regular bearer, with no crop failures observed.
Trunk:
- *Size.*—Medium, reaching a maximum diameter of 3¾" [95.3 mm.] after the eighth growing season.
- *Texture.*—Medium, shaggy.
- *Bark color.*—A Moderate yellowish brown [77. m.yBr] and Brownish gray [64. brGy] variegation with Strong brown [55. s.Br] crevices present.
- *Lenticels.*—Approximate Number Per Square Inch: 6. Color: Brownish orange [54. brO]. Average Size: ¼" [6.4 mm.] in length, 1/16" [1.6 mm.] in diameter. Shape: Eye-shaped, elongated.

Branches:
- *Size.*—Diameter of limb is 2¼" [57.2 mm.] measured 12" above the crotch, 1¾" [44.5 mm.] measured 12" above the first fork.
- *Texture.*—Smooth on first and second year wood, increasing roughness with age.
- *Color.*—1st Year Wood Topside: Grayish red [19. gy.R]. 1st Year Wood Underside: Brilliant yellow green [116. brill.YG]. 2nd Year Wood: Grayish brown [61. gy.Br]. 3rd Year Wood: A Grayish brown [61. gy.Br] and Moderate brown [58. m.Br] variegation.
- *Lenticels.*—Number Per Square Inch: More than 60 on second year wood. Color: Strong yellowish brown [74. s.yBr]. Average Size: 1/16" [1.6 mm.] in length, 1/64" [0.4 mm.] in diameter. Shape: Elongated, eye-shaped.

Leaves:
- *Size.*—Large. Average Length: 6⅛" [155.6 mm.]. Average Width: 1⅝" [41.3 mm.].
- *Arrangement.*—Alternate.
- *Thickness.*—Medium.
- *Form.*—Elliptical.
- *Apex.*—Acuminate.
- *Base.*—Rounded to acute with an average angle of 90 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: 7/16" [11.1 mm.]. Average Thickness: 1/16" [1.6 mm.]. Color: Very yellow green [115. v.YG].
- *Stipules.*—Number: 2 per leaf, up to 6 per growing tip. Average Length: 7/16" [11.1 mm.]. Color: Very yellow green [115. v.YG] becoming Strong reddish brown [40. s.rBr] with age.
- *Glands.*—Number: Mostly 2 to 6 per leaf. Position: Alternately positioned on the petiole and base of blade. Size: Medium. Form: Reniform. Color: Brilliant yellow green [116. brill.YG] becoming Deep reddish brown [41. deep rBr] in the center with age.
- *Leaf buds.*—Pointed, medium.

Flower buds:
- *Hardiness.*—Hardy, with respect to central California winters.
- *Diameter.*—Typically 5/16" [7.9 mm.] 1 week before bloom.
- *Length.*—Typically ⅝" [15.9 mm.] 1 week before bloom.
- *Form.*—Not appressed.
- *Surface.*—Pubescent.
- *Tip color.*—Light purplish pink [249. l.pPk].

Flowers: Perfect, complete, perigynous, usually a single pistil, typically thirty or more stamens, five sepal and petal locations alternately positioned.
- *Type.*—Showy, large.
- *Average flower diameter.*—2" [50.8 mm.].
- *Average flower depth.*—7/16" [11.1 mm.] when fully open.
- *Number of petals.*—Usually five, extra petal fragments commonly occur, double blossoms rarely observed.
- *Petal shape.*—Circular to oval.
- *Petal margin.*—Entire, somewhat wavy, occasional notches.
- *Average petal diameter.*—¾" [19.1 mm.].
- *Average petal length.*—13/16" [20.6 mm.].
- *Petal apex.*—Rounded.
- *Petal base.*—Rounded to somewhat truncate.
- *Petal color.*—Pinkish white [9. pkWhite] toward the apex, Light purplish pink [249. l.pPk] toward the base.

*Anther color.*—Very reddish orange [34. v.rO] over a Light yellow [86. l.Y] center at bloom onset.
*Stigma color.*—Pale yellow green [121. p.YG].
*Sepal color.*—Dark purplish red [259. d.pR] on the outer surface. The inner surface is a somewhat translucent Pinkish white [9. pk White] with both Grayish purplish red [262. gy.pR] and Vivid yellow green [115. v.YG] areas visible.
*Sepal apex.*—Rounded to elliptical to match the length and width.
*Sepal margin.*—Fairly smooth.
*Sepal outer surface.*—Pubescent.
*Sepal length.*—¼" [6.4 mm.].
*Sepal width.*—3/16" [4.8 mm.].
*Average pistil length.*—⅞" [22.2 mm.].
*Average stamen length.*—9/16" [14.3 mm.].
*Fragrance.*—Moderate.
*Blooming period.*—Medium, 5 days after 'Bright Princess' (U.S. Plant Pat. No. 14,695) peach.
*Onset of bloom.*—One percent on Feb. 27, 2012.
*Date of full bloom.*—Mar. 7, 2012.
*Duration of bloom.*—One to two weeks, dependent on ambient temperature.
*Number per cluster.*—1 to 3 with single flowers most common.

FRUIT

Maturity when described: Firm ripe, Jul. 2, 2012.
Date of first picking: Jun. 27, 2012.
Date of last picking: Jul. 4, 2012.
Size: Uniform, large.
*Average diameter axially.*—2 15/16" [74.6 mm.].
*Average diameter across suture plane.*—3 3/16" [80.9 mm.].
*Average diameter across cheek plane.*—3 1/16" [77.8 mm.].
*Typical weight.*—9.8 ounces [278 grams].
Form: Uniform, globose, symmetrical.
*Longitudinal section form.*—Round to elliptical.
*Axial view.*—Round.
Suture: Extends from the base to somewhat beyond the pistil point.
*Near the base.*—A shallow sharp groove.
*Along the side.*—A shallow trough.
*Near the apex.*—A shallow groove.
Ventral surface: Rounded, slightly buldged along the suture, lipped stronger toward the apex.
Lips: Slightly unequal.
Cavity: Flaring, elongated in the suture plane, suture showing on both sides, Brilliant yellow [83. brill.Y] stem markings typical. Depth.—¾" [19.1 mm.]. Breadth.—1⅛" [28.6 mm.].
Base: Truncate.
Apex: Rounded.
Pistil point: An inconspicuous dot, negligible in length, usually depressed within the suture, a few located on a slight nose.
Stem: Medium.
*Average length.*—⅜" [9.5 mm.].
*Average width.*—3/16" [4.8 mm.].
Skin:
*Thickness.*—Medium.
*Surface.*—Pubescent.
*Tenacity.*—Tenacious to the flesh.
*Astringency.*—Very slight.
*Tendency to crack.*—None observed in dry season.
*Color.*—Very dark red [17. v.d.R] mottled over a Moderate red [15. m.R] background.
*Down.*—Moderate, short, does not roll up when rubbed.
Flesh:
*Color.*—Brilliant yellow [83. brill.Y] with very minor Dark red [16. d.R] bleeding toward the skin and stone.
*Surface of pit cavity.*—Light yellow [86. l.Y] with some Strong red [12. s.R] broken fibers when twisted from stone.
*Amygdalin.*—Moderate.
*Juice.*—Abundant, rich.
*Texture.*—Firm, tough, melting.
*Fibers.*—Abundant, fine.
*Ripens.*—Fairly even, somewhat earlier toward the apex.
*Flavor.*—Peach flavor, acidic and sweet, typically 14 brix.
*Aroma.*—Moderate.
*Eating quality.*—Very good.

STONE

Type: Clingstone.
Form: Oval.
Hilum: Narrow.
Base: Slightly obligue, rounded.
Apex: Acuminate.
Sides: Equal.
Surface: Irregularly furrowed near the apex, pitted toward the base.
Ridges: Jagged.
External color: Deep yellowish brown [75. deep yBr].
Pit wall color when cracked: Light yellowish brown [76. l.yBr].
Cavity surface color: Moderate brown [58. m.Br] to Light yellowish brown [76. l.yBr].
Average pit wall thickness: 5/16" [7.9 mm.].
Average width: 1¼" [31.8 mm.].
Average length: 1 11/16" [42.9 mm.].
Average breadth: 1⅛" [28.6 mm.].
Tendency To split: Slight.
Kernel:
*Form.*—Oval.
*Skin color.*—Light yellow [86. l.Y] when first removed.
*Pellicle color.*—Grayish yellow [90. gy.Y].
*Vein color.*—Moderate yellow [87. m.Y].
*Taste.*—Sweet.
*Viable.*—Yes.
*Average width.*—5/16" [7.9 mm.].
*Average length.*—⅞" [22.2 mm.].
*Amygdalin.*—Scant.

USE

Market: Fresh market and long distance shipping.
Keeping quality: Good, fruit quality observed to remain in good condition after 17 days in standard cold room at 36° Fahrenheit [2° Celsius].

Shipping quality: Good.
Resistance to insects: No unusual susceptibilities noted.
Resistance to diseases: No unusual susceptibilities noted.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of peach tree, substantially as illustrated and described, that is most similar to 'Bright Princess' (U.S. Plant Pat. No. 14,695) peach by being self-fruitful, having large blossoms, having reniform leaf glands, and producing an abundance of yellow flesh peaches that are firm, that are nearly full red in skin color, and that have a sweet kernel, but is distinguished therefrom by requiring more chilling hours, by blooming later in the season, and by producing fruit that is somewhat larger in size, clingstone rather than freestone in type, and that matures about ten days later.

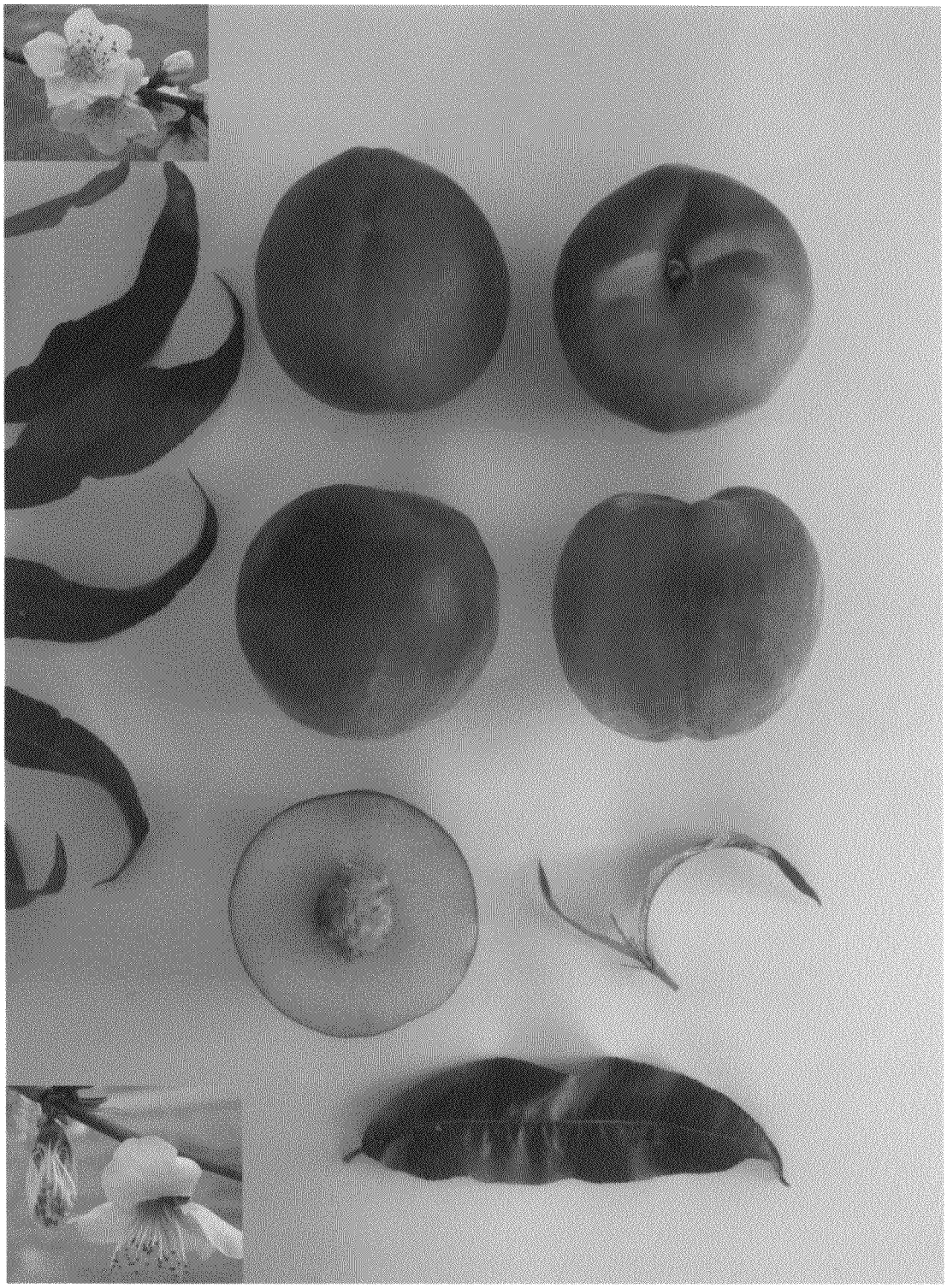

* * * * *